United States Patent
DeCenso

(10) Patent No.: US 6,997,325 B2
(45) Date of Patent: Feb. 14, 2006

(54) SYSTEM AND PROCESS FOR BREAK DETECTION IN POROUS ELEMENTS FOR SCREENING OR FILTERING

(75) Inventor: Anthony J. DeCenso, Cincinnati, OH (US)

(73) Assignee: M-I L.L.C., Houston, TX (US)

( * ) Notice: Subject to any disclaimer, the term of this patent is extended or adjusted under 35 U.S.C. 154(b) by 57 days.

(21) Appl. No.: 10/668,114

(22) Filed: Sep. 22, 2003

(65) Prior Publication Data
US 2004/0129612 A1 Jul. 8, 2004

Related U.S. Application Data

(60) Provisional application No. 60/425,669, filed on Nov. 13, 2002.

(51) Int. Cl.
B07B 1/49 (2006.01)

(52) U.S. Cl. .............. 209/401; 209/400; 209/392

(58) Field of Classification Search .......... 209/392, 209/400, 401; 455/66.1, 556.1
See application file for complete search history.

(56) References Cited

U.S. PATENT DOCUMENTS

| | | | |
|---|---|---|---|
| 3,725,666 A * | 4/1973 | Berthold | 250/559.01 |
| 4,022,693 A | 5/1977 | Morgan, Jr. | 210/345 |
| 4,251,354 A | 2/1981 | Lower | 209/240 |
| 4,582,597 A | 4/1986 | Huber | 204/313 |
| 4,613,432 A | 9/1986 | Racine | 209/254 |
| 4,655,911 A | 4/1987 | Tabor | 210/107 |
| 4,968,366 A | 11/1990 | Hukki | 156/153 |
| 5,032,210 A | 7/1991 | Hukki et al. | 156/359 |
| 5,051,171 A | 9/1991 | Hukki | 209/323 |
| 5,134,893 A | 8/1992 | Hukki et al. | 74/61 |
| 5,221,008 A | 6/1993 | Derrick, Jr. et al. | 209/269 |
| 5,226,546 A | 7/1993 | Janssens et al. | 209/319 |
| 5,242,058 A | 9/1993 | Jones | 209/403 |
| 5,255,789 A | 10/1993 | Janssens et al. | 209/319 |
| 5,265,730 A | 11/1993 | Norris et al. | 209/326 |
| 5,271,504 A | 12/1993 | Bowen et al. | 209/316 |
| 5,456,365 A | 10/1995 | Janssens et al. | 209/403 |
| 5,950,841 A | 9/1999 | Knox et al. | 209/315 |
| 5,996,807 A * | 12/1999 | Rumpf et al. | 209/401 |
| 6,089,380 A | 7/2000 | Hazrati et al. | 210/411 |
| 6,202,856 B1 | 3/2001 | Carr | 209/401 |
| 6,349,834 B1 | 2/2002 | Carr et al. | 209/366.5 |
| 6,431,368 B1 | 8/2002 | Carr | 209/403 |
| 6,513,665 B1 | 2/2003 | Hukki et al. | 209/269 |
| 6,585,116 B1 * | 7/2003 | Doelle et al. | 209/305 |

* cited by examiner

Primary Examiner—Donald P. Walsh
Assistant Examiner—Matthew J. Kohner
(74) Attorney, Agent, or Firm—Fulbright & Jaworski L.L.P.

(57) ABSTRACT

A detector for breaks in screens and filters employed in material separators includes a transmitter of RF signals and a receiver of RF signals located to either side of a screen. The separator includes a chamber having a barrier to RF signals with a path through the barrier being defined through the screen mount. The screen mount receives a screen to extend fully across the path.

16 Claims, 2 Drawing Sheets

SYSTEM AND PROCESS FOR BREAK DETECTION IN POROUS ELEMENTS FOR SCREENING OR FILTERING

PRIORITY

Applicant claims priority to U.S. Provisional Application 60/425,669, filed Nov. 13, 2002, the disclosure of which is incorporated herein by reference.

BACKGROUND OF THE INVENTION

The field of the present invention is material separation through screening or filtering and break detection for the porous elements employed.

Separator systems are used in industry for a variety of undertakings. They are used to process dry materials and liquid/solid slurries. Each one typically functions by first introducing a flow of material to a porous element such as a screen or filter, usually of woven wire mesh or a porous membrane. The flow of material is separated into two streams, one containing material that passes through the porous element, the other containing material that is rejected by the porous element. A drive mechanism may be operatively coupled with a housing to produce a vibrating motion that serves to put the material on the porous element in motion until it either passes through or is pushed off the element at the periphery thereof. Other devices use pressure to increase flow through a membrane with cycled application including reverse flow to clear the rejected material.

Such separator systems employ screens in rectangular and circular forms with screen elements tensioned on frames or with hooks tensioned on the separator itself. The screen elements range greatly in porosity and can be of a single element or of laminated elements. The separator frames can be vibratory or fixed and, when vibratory, supported by a variety of means such as springs, bushings or links. Such systems alternatively employ filters, tensioned or untensioned, supported or unsupported and of widely varying porosities and shapes including rectangular, circular, cylindrical and bag shaped. Many additional features are, of course, available such as housing covers, elaborate manifolds and various and changeable motions, rates and cycles. Patents disclosing a small sampling of such systems and components include U.S. Pat. No. 4,022,693; U.S. Pat. No. 4,251,354; U.S. Pat. No. 4,582,597; U.S. Pat. No. 4,613,432; U.S. Pat. No. 4,655,911; U.S. Pat. No. 4,968,366; U.S. Pat. No. 5,032,210; U.S. Pat. No. 5,051,171; U.S. Pat. No. 5,134,893; U.S. Pat. No. 5,221,008; U.S. Pat. No. 5,226,546; U.S. Pat. No. 5,242,058; U.S. Pat. No. 5,255,789; U.S. Pat. No. 5,265,730; U.S. Pat. No. 5,271,504; U.S. Pat. No. 5,456,365; U.S. Pat. No. 5,950,841; U.S. Pat. No. 6,089,380; U.S. Pat. No. 6,202,856; U.S. Pat. No. 6,349,834; U.S. Pat. No. 6,431,368; and U.S. Pat. No. 6,513,665, the disclosures of which are incorporated herein by reference.

Materials typically screened vary considerably in their particle size, bulk density, chemical composition, temperature, moisture content and other physical and chemical characteristics. Any particular separator system in a given processing plant is likely dedicated to handling a single material with consistent properties. Examples of such materials, to show the diversity but not to provide a comprehensive list, include:

| | |
|---|---|
| abrasives | activated carbon |
| calcium carbonates | ceramic slurries |
| chlorine compounds | citric acid |
| fertilizers | flours |
| food products | gunpowder |
| minerals | paper coating slurries |
| pharmaceuticals | pigments |
| polystyrene beads | powdered metals |
| powdered paints | printing inks |
| PVC powder | refractories |
| rocket propellants | starches |

As a result, various screen configurations, vibration profiles and environments are employed to maximize efficiency and the quality of the resulting processed materials.

By far the most common failure mode for separator systems is the failure of the porous element. Screens, for example, are typically made of finely woven wire cloth drawn taut by a screen frame or tensioning apparatus on the separator. Failure is caused by numerous factors such as wear and fatigue failure. Such failures typically occur as breaks in the screening media itself resulting in a damaged screen. Such breaks may manifest themselves as tears (a series of mutually adjacent broken wires), punctures (tears in two directions) or holes (missing portions of the screening material). Once the screen has failed, the function of a separating system is compromised. At a minimum, it can no longer be relied upon to reject all oversized material because such material can now pass through the break in the screen. Worse, it can result in fragments of the failed screen contaminating the material being screened, presenting a serious hazard in food or pharmaceutical screening operations. Similar failure occur in filter elements.

As the porous elements are typically located within closed housings or under material being processed, it is difficult to visually detect such failures. Thus, where critical separation is demanded, frequent inspection is advisable. As such efforts to insure quality separation result in downtime and labor and still result in compromised processed material, methods for detecting breaks have been long sought. Systems have been devised that attempt to detect screen failure by measuring the electrical or optical paths through the mesh screen itself. See U.S. Pat. No. 5,996,807, the disclosure of which is incorporated herein by reference. These are believed to have been proven impractical and have not met with general market acceptance.

SUMMARY OF THE INVENTION

The present invention is directed to a detector of breaks in porous elements for separator systems and the process of such detection. A transmitter of an RF signal is placed to one side of a porous element mount while a receiver of the RF signal is placed to the other. Breakage resulting in holes large enough to let the RF signal through the porous element then result in a signal to the receiver indicating failure.

In a first separate aspect of the present invention, the detector includes a chamber having a barrier to the RF signal with a path through the barrier. A porous element mount is arranged to receive a porous element fully across the path through the barrier. The RF signal transmitter and the RF signal receiver are placed with one inside the chamber and the other outside the chamber.

In a second separate aspect of the present invention, the detector is part of a separator system including an elastically mounted housing and a vibration generator operatively attached to the housing. A chamber has a barrier to the RF signal with a path through the barrier. A porous element mount is arranged to receive an element fully across the path through the barrier. The RF signal transmitter and the RF signal receiver are placed with one inside the chamber and the other outside the chamber.

In a third separate aspect of the present invention, the systems of the first and second aspect are contemplated to include an electrically conductive porous element extending fully across the path through the barrier. The RF signal is at least substantially attenuated in passing through preconfigured interstices in the undamaged element. The electrically conductive element may include metal screen cloth.

In a fourth separate aspect of the present invention, a process for detecting breaks in a porous element contemplates processing material through a separator, transmitting an RF signal at the porous element of the separator, shielding the other side of the porous element from the RF signal and sensing the presence of the RF signal above a threshold indicating porous element breakage. The generation of the signal may be continuous or may be intermittent with or without voiding the separator of processing material during generation of the signal.

In a fifth separate aspect of the present invention, any of the foregoing aspects are contemplated to be employed in greater combination to greater advantage.

Accordingly, it is an object of the present invention to provide a useful porous element breakage detection system. Other and further objects will appear hereinafter.

DETAILED DESCRIPTION OF THE PREFERRED EMBODIMENT

Figure 1:
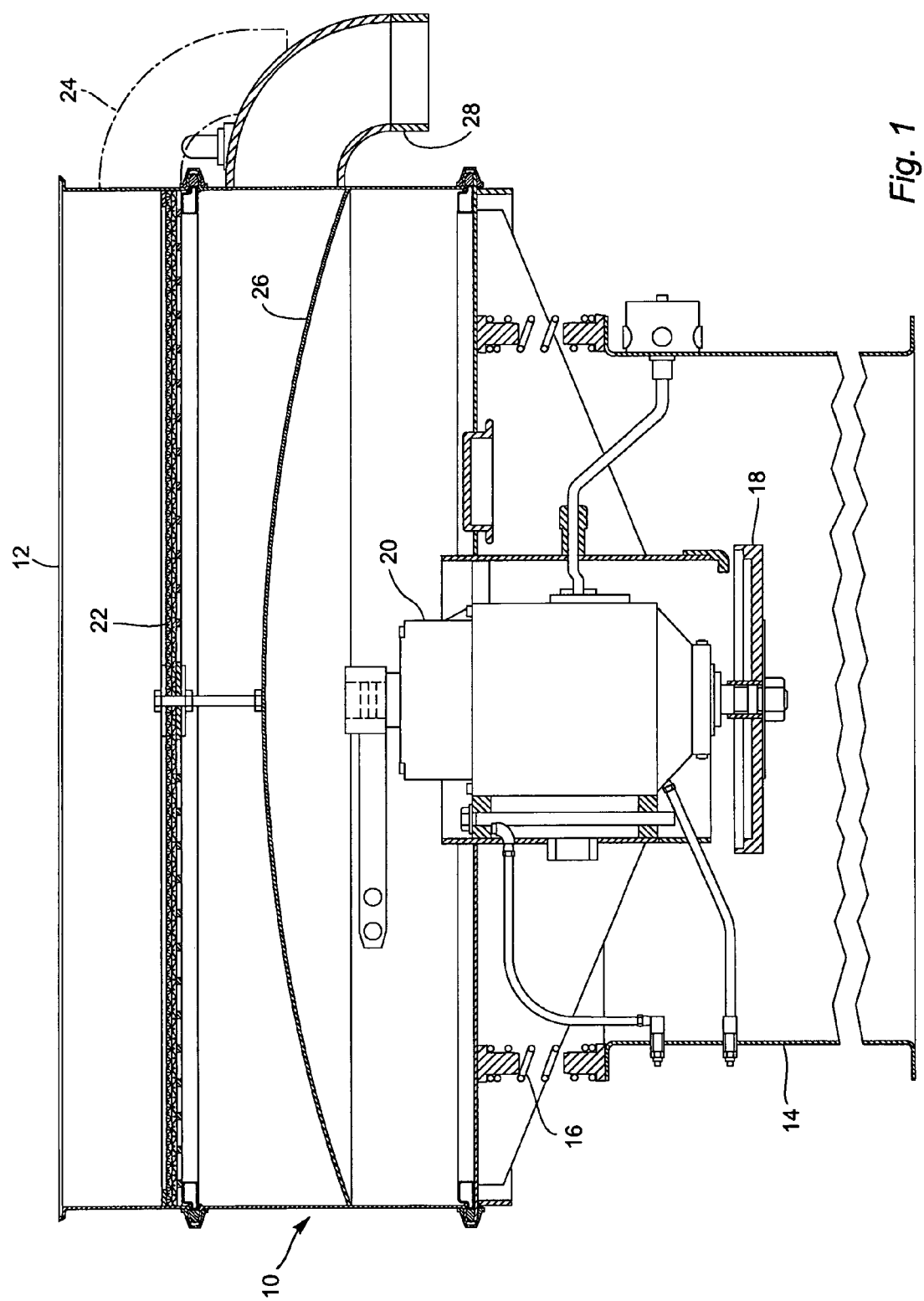
FIG. 1 is a cross-sectional view of a vibratory material separator with which a detector may be employed.

Turning in detail to the drawings, FIG. 1 illustrates a conventional vibratory screen material separator, generally designated 10, to provide context for one material separation system for detecting breaks in a porous element. Nonvibratory screening systems and filtration systems in a range of such systems described above in the Background of the Invention can also find increased utility with a system for detecting breaks in the porous element employed for material separation.

The separator 10 includes a housing 12 which is elastically mounted to a base 14 on springs 16. A vibration generator 18 driven by a motor 20 causes the elastically mounted housing 12 to vibrate at an advantageous frequency and amplitude for material screening or filtering. A porous element, which is a screen 22 in this embodiment, extends across the housing 12 to separate material deposited thereon by selected characteristics. Above the screen 22 is an overs outlet 24 while below the screen 22 is a domed manifold 26 which feeds a throughs outlet 28.

Figure 3:
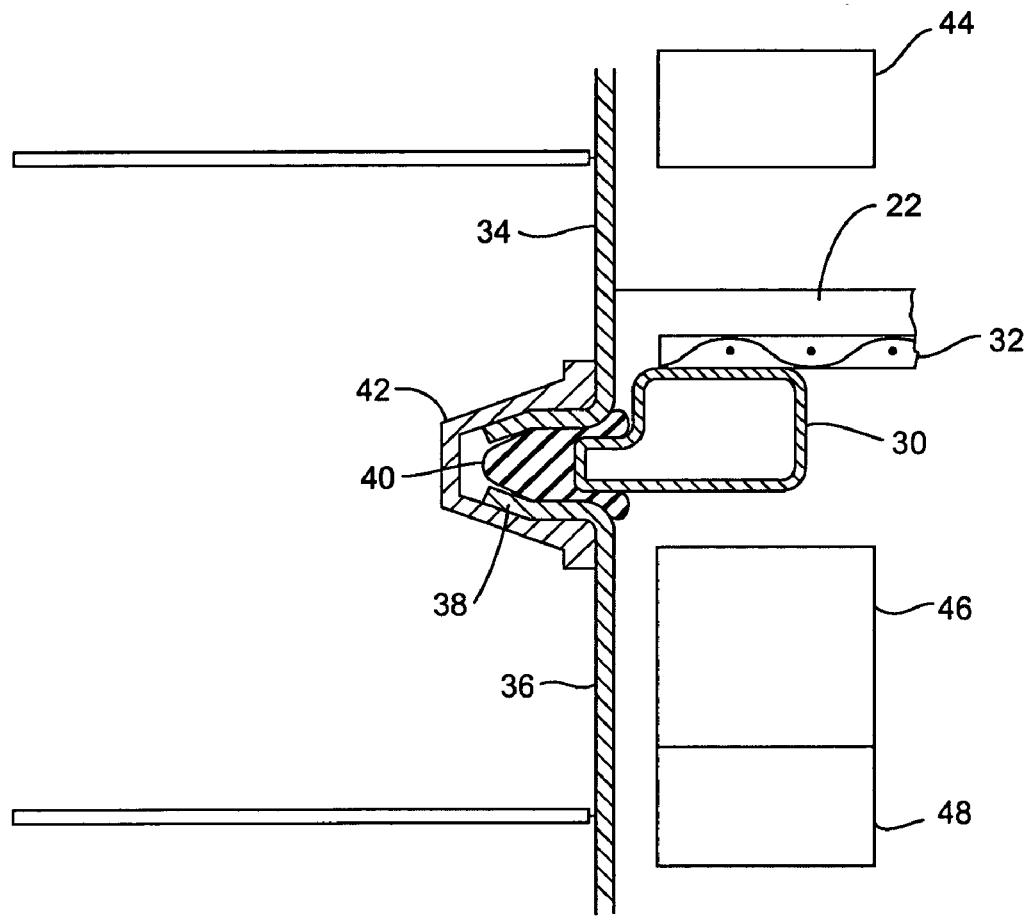
FIG. 3 is a housing seal arrangement associated with the devices of FIGS. 1 and 2

Referring to FIG. 3, the seal arrangement and construction of the housing 12 about the screen 22 is illustrated. Also illustrated are details of the porou8s element, defined in this embodiment as a screen 22. The screen 22 includes a screen frame 30 which may be a formed metal ring. Screen cloth 32 is bonded to the screen frame 30 in a taut state. The screen cloth 32 is typically wire mesh of electrically conductive stainless steel. Preconfigured interstices are defined by the weave, the wire diameter and the wires per unit measure.

The housing 12 is shown to be of at least two cylindrical housing elements 34 and 36. These elements 34 and 36 come together about a flange 38 on the screen frame 30. As such, a screen mount is defined therebetween fully about the interior of the housing 12. A gasket 40 is positioned about the flange 38 and a clamp band 42 draws the entire assembly together. The entire separator 10 also is contemplated to include a cover with an inlet therein through which material is delivered to the screen 22.

In creating a chamber within the housing 12 which includes a barrier to an RF signal, the housing components 34 and 36 are electrically conductive. The cover (not shown) might also be electrically conductive as well as the domed manifold 26 beneath the screen 22. The overs outlet 24 and the throughs outlet 28 can also be electrically conductive and further electrically conductive shielding as may be needed is contemplated to prevent transmission of the RF signals therethrough. Further, the gasket 40 is anticipated to be electrically conductive or to require an electrically conductive barrier to prevent the RF signals from flowing around the screen frame 30 within the screen mount. The conductivity is provided through the employment of sheet metal components acting to create a barrier to the RF signals.

With the aforementioned components, the housing 12 may define a chamber having a barrier to the RF signals either above or below the screen 22. Below the screen 22, the housing element 36, the domed manifold 26, the throughs outlet 28 and the gasket 40, along with other shielding as may be required, define a first chamber. The upper housing element 34, the overs outlet 24, the gasket 40 and a cover (not shown), again with additional shielding as may be needed, may define a second chamber with a barrier to the RF signals.

Between these two defined spaces, whether both form a chamber or only one forms a chamber with an RF barrier, a path exists through the screen mount. Without the screen 22, material to be processed has a clear path. So do the RF signals. The screen 22, positioned across this path in the screen mount defined by the housing 12 creates a selective path for material being processed according to selected characteristics. By selecting the appropriate RF signal, the screen 22 of conductive metal wire can act as a barrier to substantially attenuate, including to the point of virtual elimination, the RF signal passage along the path across the screen 22 so long as the preconfigured interstices of the unbroken screen remain intact. The screen 22 having interstices in the range of commercial screening systems is a barrier to RF signals in the microwave range. Other porous elements including screens and membranes which block microwaves in addition to woven wire screen cloth can be employed. As one example, electrically conductive coating on nonconductive substrates may adequately block RF signals in the appropriate range.

In the preferred embodiment, the porous element defined by the screen 22, which embodies a barrier across the path to the chamber, is shown to extend in a plane. Instead, the porous element may extend into or out from the main volume of a defined chamber as a filter bag or a cylinder, for example, and the path may, therefore, not necessarily be linear but passes through a porous element mount with the porous element extending fully across the path. The frame retaining the edges of the porous element may be fixed to the porous element as with the screen 22 or may be a mechanism with the housing, thus becoming part of the porous element mount.

Figure 2:
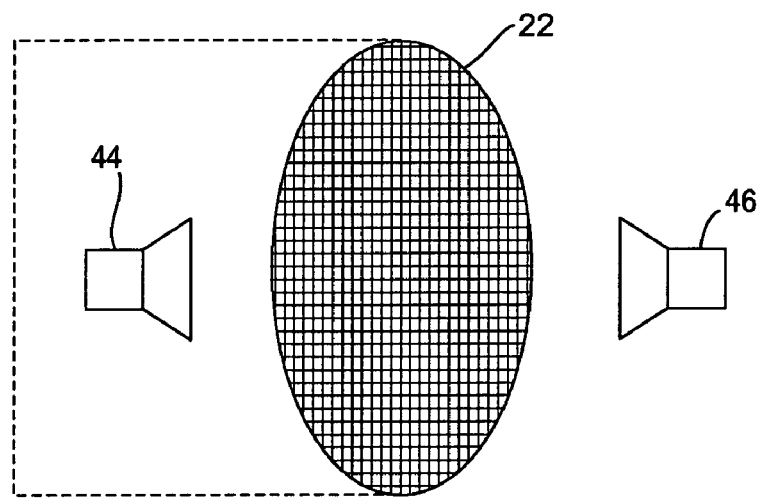
FIG. 2 is a schematic view of a detector as associated with the separator of FIG. 1.

A signal system, illustrated in FIG. 2 schematically, is employed with the vibratory material separator 10 to define a separator system. The signal system includes a signal transmitter 44 and a signal receiver 46 located to either side of the screen 22. The transmitter 44 and the receiver 46 may be mounted to or relative to the housing components 34 and 36, respectively. The signal system and the components thereof operate in the RF (radio frequency) range and, more practically given the size of the preconfigured interstices of commercial screens 22, operate in the higher end of the RF range in the microwave range, with the signal system, the transmitter 44 and the receiver 46 being microwave elements. The signals are understood to fall in the range of 700 megaHz to 50 gigaHz with specific empirical tuning to match the characteristics of the screen 22 employed.

Also associated with the microwave signal receiver 46 is a signaling source 48. The signaling source 48 receives input from the receiver 46 and is actuated by the receiver 46 when the receiver 46 receives the microwave signal above a threshold. The threshold is established such that the signaling source 48 does not respond to any substantially attenuated signal passing through a screen 22 without breaks. At the same time, the threshold must also be such that the signaling source 48 is activated when a significant break occurs in the screen 22. Leakage of the RF signal around the screen 22 is to be reduced such that a threshold can be meaningfully set to be activated by a significant break. A significant break in the screen 22 is one that degrades the quality of the throughs resulting from the screening process and is more or less critically significant depending on the material processed. In the case of pharmaceuticals, the quality requirements are far stricter for the end product than in food processing, for example, and degradation in quality is measured by a more critical standard.

When the integrity of the barrier defined by the porous element, in this case the screen 22, fails in any manner which increases an opening size, the length of the resulting opening approaches the wave length of a microwave signal to the point where transmission through that opening can occur. Experiments have shown that detection is likely with the opening achieving one-quarter the wavelength. Screen failures are detected by exploiting this relationship between microwave transmission and electrically conductive barriers.

The signal source 48 recognizes the change in a physical state of the screen 22 when a break occurs through the received RF signal to the receiver 46 and generates a signal as may be desired by the operator, to sound an alarm, to open the power switch to the separator, etc.

In operation the process for detecting breaks during processing of material through the material separator 10 includes the transmission of an RF signal most appropriately in the microwave range and tuned to the RF barrier characteristics of the porous element, the screen 22 in this embodiment, on the first side thereof. The transmitter 44 operates at a frequency with a wave length that is longer than the preconfigured interstices in the screen 22 such that an intact screen will significantly attenuate the signal. Such a differential may be an order of magnitude. With the screen 22 intact, the receiver 46 can be used to define the base line signal transmission characteristics to establish an appropriate threshold. Once a failure has occurred in the screen 22, the resulting enlarged opening will reduce the screen's attenuation of the microwave signal. This allows a stronger signal to reach the receiver 46. Through the use of either analog or digital signal processing techniques, this difference in signal strength is detected and appropriate alarms activated so that the screening process operator can take corrective action Preferably, the microwave system operates continuously and is able to announce a fault as soon as it occurs. While this is preferred, it is not always necessary given that in most processing operations immediate corrective action (such as stopping the line) is not possible. The system can be put to effective use in an intermittent monitoring mode such that it identifies the occurrence of a screen failure within a relative short period of time after its actual occurrence. This time value will vary by industry, but a matter of minutes is sufficient for practically all applications.

Preferably, measurements are made while the separator 10 is operating. In doing so, the microwave system and the screen 22 that is being monitored will be subjected, in conventional equipment, to a magnitude of approximately 2 to 4 G's at a frequency of 4 to 30 Hz. depending on the separator used. Alternatively, the separator 10 could be stopped briefly while a measurement is taken.

It is also preferred that measurements be made while the separator 10 is processing material. While doing so, the screen 22 may be covered with material to various depths. With most materials, the RF signal will be able to pass through these depths and not be affected to the point that the signal will not be effective. With problematic materials, inflow to the separator 10 may be turned off while the separator 10 continues to operate. In this way, the processed material is flushed out before a measurement is taken.

In setting up the system, shielding is undertaken. Inherently, separators 10 provide a substantial amount of shielding as they are constructed almost entirely of electrically conductive material such as stainless steel alloys. Sealing about the screen 22 is conventional. However, the seals 40 are typically elastomeric. Further, the ports associated with the overs outlet 24 and throughs outlet 28 provide electrically conductive paths, along with the elastomeric seals 40, for circumventing the path through the screen 22. Electrically conductive material molded into gasket and discharge components, replacement of such components by electrically conductive devices or shielding around these devices themselves can provide adequate signal attenuation such that the receiver 46 can distinguish between screens 22 which are intact and those which have experienced a significant break. Depending on the materials processed, additional events may be sensed such as screen blinding.

Thus, a screening or filtering system capable of detecting breaks is disclosed. While embodiments and applications of this invention have been shown and described, it would be apparent to those skilled in the art that many more modifications are possible without departing from the inventive concepts herein. The invention, therefore is not to be restricted except in the spirit of the appended claims.

What is claimed is:

1. A detector of breaks in porous elements for a material separator, comprising
    a transmitter of an RF signal;
    a receiver of the RF signal;
    a chamber including a barrier to the RF signal and a path through the barrier, the path being capable of allowing the RF signal and the material to move therethrough, one of the transmitter and the receiver being inside the chamber and the other of the transmitter and the receiver being outside the chamber;
    a porous element mount fully about the path.

2. A detector of breaks in porous elements for a material separator, comprising
- a transmitter of an RF signal;
- a receiver of the RF signal;
- a chamber including a barrier to the RF signal and a path through the barrier, the path being capable of allowing the RF signal and the material to move therethrough, one of the transmitter and the receiver being inside the chamber and the other of the transmitter and the receiver being outside the chamber;
- a porous element mount fully about the path, the RF signal being in the microwave range of RF electromagnetic energy.

3. The detector of claim 1 further comprising
an electrically conductive porous element fixable in the porous element mount to extend fully across the path, the electrically conductive porous element including preconfigured interstices therethrough, the RF signal being at least substantially attenuated in passing through the preconfigured interstices.

4. The detector of claim 1 further comprising
a screen fixable in the porous element mount to extend fully across the path, the screen including a screen frame and metal screen cloth with preconfigured interstices therethrough, the RF signal being at least substantially attenuated in passing through the preconfigured interstices.

5. A material separator comprising
- a housing including a material inlet, an overs outlet and a throughs material outlet;
- a transmitter of an RF signal;
- a receiver of the RF signal;
- a chamber in the housing including a barrier to the RF signal and a path through the barrier, the path being capable of allowing the RF signal and the material to move therethrough, one of the transmitter and the receiver being inside the chamber and the other of the transmitter and the receiver being outside the chamber, the material inlet and the overs outlet being one of inside and outside the chamber and the throughs outlet being the other of inside and outside the chamber;
- a porous element mount fully about the path.

6. A material separator comprising
- a housing including a material inlet, an overs outlet and a throughs material outlet;
- a transmitter of an RF signal;
- a receiver of the RF signal;
- a chamber in the housing including a barrier to the RF signal and a path through the barrier, the path being capable of allowing the RF signal and the material to move therethrough, one of the transmitter and the receiver being inside the chamber and the other of the transmitter and the receiver being outside the chamber, the material inlet and the overs outlet being one of inside and outside the chamber and the throughs outlet being the other of inside and outside the chamber;
- a porous element mount fully about the path, the RF signal being in the microwave range of RF electromagnetic energy.

7. The separator of material of claim 5 further comprising an electrically conductive porous element fixable in the porous element mount to extend fully across the path, the electrically conductive porous element including preconfigured interstices therethrough, the RF signal being at least substantially attenuated in passing through the preconfigured interstices.

8. The separator of material of claim 5 further comprising
a screen fixable in the porous element mount to extend fully across the path, the screen including a screen frame and metal screen cloth with preconfigured interstices therethrough, the RF signal being at least substantially attenuated in passing through the preconfigured interstices.

9. A separator system for separating material by a characteristic into segregated components, comprising
(a) a separator having a wire mesh screen with preconfigured interstices for receiving the material, a throughs outlet for directing segregated material from the vibratory separator which passes through the preconfigured interstices and an overs outlet for directing oversized material which does not pass through the preconfigured interstices; and
(b) a microwave system having (i) a microwave signal transmitter mounted in the vibratory separator for emitting a microwave signal with a wavelength frequency such that signal strength is significantly attenuated by the undamaged wire screen, (ii) a microwave signal receiver mounted in the vibratory separator, and (iii) a signaling source operably connected to the microwave signal receiver,
whereby significant microwave energy from the microwave signal emitted from the transmitter is not allowed to pass through the wire mesh screen unless the integrity of the wire mesh screen is damaged thereby allowing significant microwave energy from the microwave signal emitted from the transmitter to pass therethrough and be received by the receiver, activating the signaling source to alert an operator of the separator system.

10. A process for detecting breaks in a porous element for a material separator, comprising
- processing material through a separator;
- at least periodically transmitting an RF signal at the first side of the porous element in the separator;
- shielding the other side of the porous element from the RF signal;
- sensing the presence of the sent RF signal above a threshold on the shielded other side of the porous element;
- activating a signaling source upon detecting an RF signal above the threshold.

11. The process of claim 10 further comprising turning off inflow of the material prior to sensing the presence of the sent RF signal.

12. The process of claim 10, transmitting the RF signal being continuous.

13. A detector of breaks in porous elements for a material separator, comprising
- a transmitter of an RF signal;
- a receiver of the RF signal;
- a chamber including a barrier to the RF signal and a path through the barrier, the path being capable of allowing the RF signal and the material to move therethrough, one of the transmitter and the receiver being inside the chamber and the other of the transmitter and the receiver being outside the chamber;
- a porous element mount to receive a porous element fully across the path.

14. The detector of claim 13, the RF signal being in the microwave range of RF electromagnetic energy.

15. A material separator comprising
- a housing including a material inlet, an overs outlet and a throughs material outlet;
- a transmitter of an RF signal;

a receiver of the RF signal;

a chamber in the housing including a barrier to the RF signal and a path through the barrier, the path being capable of allowing the RF signal and the material to move therethrough, one of the transmitter and the receiver being inside the chamber and the other of the transmitter and the receiver being outside the chamber, the material inlet and the overs outlet being one of inside and outside the chamber and the throughs outlet being the other of inside and outside the chamber;

a porous element mount to receive a porous element fully across the path.

16. The separator of material of claim 15, the RF signal being in the microwave range of RF electromagnetic energy.

\* \* \* \* \*